(12) United States Patent
Narasimhan et al.

(10) Patent No.: US 7,106,327 B2
(45) Date of Patent: Sep. 12, 2006

(54) SYSTEMS AND METHODS FOR MODELING THE IMPACT OF A MEDIUM ON THE APPEARANCES OF ENCOMPASSED LIGHT SOURCES

(75) Inventors: Srinivasa Narasimhan, New York, NY (US); Shree Nayar, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 227 days.

(21) Appl. No.: 10/723,084

(22) Filed: Nov. 26, 2003

(65) Prior Publication Data

US 2005/0073682 A1   Apr. 7, 2005

Related U.S. Application Data

(60) Provisional application No. 60/429,301, filed on Nov. 26, 2002.

(51) Int. Cl.
*G06T 15/50* (2006.01)
*G06T 15/60* (2006.01)

(52) U.S. Cl. .................... 345/426; 382/254
(58) Field of Classification Search ............. 345/426
See application file for complete search history.

(56) References Cited

U.S. PATENT DOCUMENTS

| | | | |
|---|---|---|---|
| 3,510,225 A | 5/1970 | Collis et al. | |
| 3,519,354 A | 7/1970 | Brown et al. | |
| 3,640,626 A | 2/1972 | Liskowitz | |
| 3,668,674 A | 6/1972 | Westendorf | |
| 3,758,211 A | 9/1973 | Bateman et al. | |
| 5,075,856 A | 12/1991 | Kneizys et al. | |
| 5,239,352 A | 8/1993 | Bissonnette | |
| 5,452,723 A | 9/1995 | Wu et al. | |
| 5,884,226 A * | 3/1999 | Anderson et al. | ............. 702/3 |
| 6,459,818 B1 * | 10/2002 | George | ..................... 382/254 |

(Continued)

FOREIGN PATENT DOCUMENTS

EP     1 022 549 A1     7/2000

OTHER PUBLICATIONS

Evans, K. F., The Spherical Harmonics Discrete Ordinate Method for Three-Dimensional Atmospheric Radiative Transfer, Feb. 1, 1998, Journal of the Atmospheric Sciences, vol. 55, pp. 429-446.*

(Continued)

*Primary Examiner*—Ulka Chauhan
*Assistant Examiner*—Said Broome
(74) *Attorney, Agent, or Firm*—Wilmer Cutler Pickering Hale and Dorr LLP

(57) ABSTRACT

The present invention provides systems and methods for modeling the impact of a medium on the appearances of encompassed light sources using a Legendre polynomial series solution to a Radiative Transfer Equation for Spherical Media (RTE-SM) called an Atmospheric Point Spread Function (APSF). Using this APSF, it is possible to determine characteristics of the medium causing the multiple scattering of the light from the encompassed light source. For example, by observing a street light in bad weather at night, using the APSF, it is possible to determine whether the bad weather is haze, mist, fog, or rain. Similarly, the APSF may be used to estimate the size of particles in a liquid. It is also possible using the APSF to remove and/or add an effect of the medium on a light source captured in an image.

65 Claims, 10 Drawing Sheets

U.S. PATENT DOCUMENTS 6,721,051 B1 * 4/2004 Mengu.cedilla. et al. ... 356/368

OTHER PUBLICATIONS

Abel, T. and Wandelt, B.D., 2001, "Adaptive Ray Tracing for Radiative Transfer Around Point Sources", Mon. Not. R. Astron. Soc., 000, 000-000 1-5.

Ambartsumian, V., 1945, "A point source of light within a scattering medium", Bulletin of theErevan Astronomical Observatory 6, 3.

Beckman et al., 1994, "Intraocular light scattering in vision, artistic painting, and photography", Applied Optics 33,21.

Bissonnette, L.R., 1988, "Multiscattering Model for Propagation of Narrow Light Beams in Aerosol Media", Applied Optics, 27(12):2478-2509.

Bissonnette, L.R., et al., 1988, "Transmitted Beam Profiles, Integrated Backscatter, and Range-Resolved Backscatter in Inhomogeneous Laboratory Water Droplet Clouds", Applied Optics, 27(12):2485-2494.

Blasi et al., 1993, "A rendering algorithm for discrete volume density objects", Computer Graphics Forum 12,3,201-210.

Bradley et al., 2000, "Measurements of rainfall properties using long optical path imaging", J. of Atmospheric and Oceanic Technology, 17: 761-772.

Chandrasekhar, S., 1944, "On the Radiative Equilibrium of a Stellar Atmosphere. V", American Astronomical Society, 95-107.

Chitanvis, S.M., et al., "Effect of Thermal Blooming on Pulse Propagation Through Vaporizing Aerosols", Applied Optics 27(12):2495-2501.

Cozman, F. et al., "Depth from Scattering", Robotics Institute, Carnegie Mellon University, Pittsburgh.

Dorsey et al., 1999, "Modeling and rendering of weathered stone", SIGGRAPH 99, 225-34.

Ebert and Parent, 1990, Rendering and animation of gaseous phenomena by combining fast volume and scaline a-buffer techniques, SIGGRAPH 90. 357-66.

Elliott, 1955, "Milne's problem with a point source", Proc. Of Royal Soc. Of London, Series A., Mathematical and Physical Sciences 228, 1174.

Fang et al., 1995, "The coronal aureole", Astonomy and Astrophysics, 293.

Grewe, L. et al. 1998, "Atmospheric Attenuation Reduction Through Multi-Sensor Fusion", SPIE, 3376:102-109.

Hanrahan and Krueger, 1993, "Reflection from layered surfaces due to subsurface scattering", SIGGRAPH 93. 165-74.

Henyey et al., 1941, "Diffuse radiation in the galaxy", Astrophysics Journal 93, 70-83.

Ishimaru, A., 1978, "Limitation on Image Resolution by a Random Medium", Applied Optics, 17(3): 348-352.

Jaffe, J., 1990, "Computer Modeling and the Design of Optimal Underwater Imaging Systems", IEEE Journal of Oceanic Engineering, 15(2): 101-111.

Jaffe, J., 1995 "Monte Carlo Modeling of Underwater-Image Formation: Validity of the Linear and Small-Angle Approximations", Applied Optics, 34(24): 5413-5421.

Jensen et al., "A Physically-Based Night Sky Model", To appear in the SIGGRAPH conference proceedings.

Jensen et al., "Efficient Simulation of Light Transport in Scenes with Participating Media Using Photon Maps.", Mental Images GmbH & Co. KG, Fasanenstraβe 81, D-10623 Berlin, Germany.

Jensen et al., 2001, "A practical Model for subsurface light transport", SIGGRAPH 01. 511-18.

Kajiya and Herzen, 1984, Ray tracing volume densities. SIGGRAPH 84. 165-174.

Koenderink and Van Doorn, 2001, "Shading in the case of translucent objects", Human Vision and Electronic Imaging VI, Rogowitz, Pappas, eds., SPIE. 312-320.

Kopeika, N. , 1981, "General wavelength dependence of imaging through the atmosphere", 20,9.

Kwan, W.C. et al., 1999, "Iterative Methods for Phase Diversity-based Blind Deconvolution in Atmospheric Optics", Department of Mathematics, The University of Hong Kong, 0-7803-5467-2/99 IEEE.

Languenou et al., 1994, "Global illumination in presence of participation media with general properties", Eurographics Rendering Workshop, 69-85.

Linskens and Bohren, 1994, "Appearance of the Sun and the moon seen through clouds", Applied Optics, 33 (21).

Lutomirski, R.F., 1978, "Atmospheric Degradation of Electrooptical System Performance", Applied Optics, 17(24): 3915-3921.

Marshak, R., 1947, "Note on the spherical harmonic method as applied to the milne problem for a sphere", Physical Review 71(7): 443-446.

Max, N., 1994, "Efficient light propagation for multiple anisotropic volume scattering", Eurographics Rendering Workshop, 87-104.

McCormick , N.J. et al., 2000, "Isotropic Spherical Source Analysis for Ocean Optics", Applied Optics, 39(27):4902-4910.

Mitsunaga and Nayar, 1999, "Radiometric Self Calibration", Proc. Of CVPR, I:374-380.

Nakamae et al., 1986, "Montage: the overlaying of the computer generated image onto a background photograph", 20,3:207-14.

Nakamae et al., 1990, "A lighting model aiming at drive simulators", SIGGRAPH 90.395-404.

Narasimhan and Nayar, 2000, "Chromatic framework for vision in bad weather", Proc. CVPR.

Narasimhan and Nayar, 2001, "Removing weather effects from monochrome images", Proc. CVPR.

Narasimhan et al., 2002, "All the images of an outdoor scene" Proc. ECCV.

Narasimhan and Nayar, Aug. 2002, "Vision and the atmosphere", 28, 3.

Nayar and Narasimhan, 1999, "Vision in bad weather", Proc. ICCV.

Nishita and Nakamae, 1987, "A shading model for atmosphere scattering considering luminous intensity distribution of light sources", 21, 3, 303-310.

Nishita et al., 1996, "Display of clouds taking into account multiple anisotropic scattering and sky light", SIGGRAPH 96.379-386.

Oakley and Satherley, 1998, "Improving image quality in poor visibility conditions using a physical model for degradation", IEEE Trans. On Image Processing, Feb. 7.

Pattanaik and Mudur, 1993, "Computation of global illumination in a participating medium by monte carlo simulation", J. of Visualization and Computer Animation, 4, 3, 133-152.

Pharr and Hanrahan, 2000, "Monte Carlo Evaluation of non-linear scattering equations for subsurface reflection", SIGGRAPH 00. 75-84.

Reinersman, P.N. et al., 1995, "Monte Carlo Simulation of the Atomspheric Point-Spread Function With an Application to Correction for the Adjacency Effect", Applied Optics, 34(21):4453-4471.

Rushmeier and Torrance, 1987, "The zonal method for calculating light intensities in the presence of a participating medium", SIGGRAPH 87. 293-302.

Sakas, G., 1990, "Fast rendering of arbitrary distributed volume densities", Eurographics 90. 519-530.

Schechner et al., 2001, "Instant Dehazing of Images Using Polarization", Proc. CVPR.

Schuster, A., 1905, "Radiation Through A Foggy Atmosphere", The Astrophysical Journal, 21(1):1-22.

Spencer et al., 1995, "Physically based glare effects for digital images", SIGGRAPH 95. 325-334.

Stam , J., 1995, "Multiple scattering as a diffusion process", Eurographics Rendering Workshop 41-50.

Stamnes, K., et al., 1988, "Numerically Stable Algorithm for Discrete-Ordinate-Method Radiative Transfer in Multiple Scattering and Emitting Layered Media", Applied Optics 27(12):2502-2509.

Suen, P., et al., 2001, "The Impact of Viewing Geometry on Vision Through the Atmosphere", Electrical and Computer Engineering University of California, IEEE 0-7695-1143-0/01, 454-459.

Tan, K. et al., 2000, "Enhancement of Color Images in Poor Visibility Conditions", Department of Electrical Engineering and Electronics UMIST, IEEE 0-7803-6297-7/00, 788-791.

Voss, K.J. and Chapin, A.L., 1990, "Measurement of the Point Spread Function in the Ocean", Applied Optics, 29(25): 3638-3642.

Zardecki, A. and Deepak, A., 1983, "Forward Multiple Scattering Corrections as a Function of Detector Field of View", Applied Optics, 22(19): 2970-2976.

Zardecki, A., et al., 1986, "Two- and Three-Dimensional Radiative Transfer in the Diffusion Approximation", Applied Optics, 25(19): 3508-3515.

* cited by examiner

SYSTEMS AND METHODS FOR MODELING THE IMPACT OF A MEDIUM ON THE APPEARANCES OF ENCOMPASSED LIGHT SOURCES

CROSS REFERENCE TO RELATED APPLICATION

This application claims the benefit of U.S. Provisional Patent Application No. 60/429,301, filed Nov. 26, 2002, which is hereby incorporated by reference herein in its entirety.

STATEMENT REGARDING FEDERALLY SPONSORED RESEARCH OR DEVELOPMENT

The invention was made with United States Government support under National Science Foundation Contract No. IIS-99-87979 and DARPA Human ID Program Contract N00014-00-1-0916, and the United States Government may have certain rights in the invention.

FIELD OF THE INVENTION

Generally speaking, the present invention relates to systems and methods that model the impact of a medium on the appearances of encompassed light sources. More particularly, the present invention relates to systems and methods which model multiple scattering of light from a light source encompassed by the medium, and that may then determine characteristics of the medium or alter images of the light source to remove or add effects of the medium.

BACKGROUND OF THE INVENTION

Arguably, nothing in the world impacts the daily lives of people more than the weather.

Perhaps nowhere is the effect of weather more strongly felt than on the runways of world's airports. Haze, mist, fog, and rain can and do prevent airplanes from being able to take off and land. Not only do these weather conditions present an inconvenience to travelers in the form travel delays, these conditions can be life threatening when fog, for example, makes it impossible for an airline pilot to see the runway. Naturally, such weather conditions also impact life in countless other ways as well.

Because of these effects, researchers have attempted to build machines and develop models that can accurately gauge the weather. For example, at many airports, visibility meters have been put in place for determining the visibility at discrete locations around the grounds of the airport. Such machines detect the impact of atmospheric conditions (such as fog) on a beam of light transmitted from a light source, such as a laser, to a detector. These machines rely on the principle that particles in the atmosphere scatter light incident on those particles. Such machines are problematic, however, in that they only sample light in a small region (e.g., a two foot by two foot region) and are based on single scattering. Moreover, because of the complexity of these machines, they are quite expensive.

In contrast to the single scattering principle used in these machines is the principle of multiple scattering. One easily understood illustration of multiple scattering is the manner in which bad weather impacts the appearance of light sources, especially when viewed at night. This impact is typically seen in the form of a glow or halo that appears to surround a light source. The appearance of this glow or halo is the result of light rays being deflected multiple times by particles in the atmosphere as they leave the light source, such that the rays appear to be originating from an area surrounding the light source.

Attempts have been made to model the effects of multiple scattering on light rays in the atmosphere. For example, one approach has been to assume that the paths of light traversal are random and then to apply numerical Monte-Carlo techniques for ray tracing. Monte-Carlo techniques are problematic, however, in that they attempt to predict the paths of light based upon each photon impacting each particle in the medium. Such an approach is highly dependent upon the specific properties of the medium, such as the density of the medium, type of particles in the medium, the size of the medium, etc. As a consequence of this, millions of rays must be traced through the atmosphere to accurately model the multiple scattering using Monte-Carlo techniques. Thus, when attempting to model a single light source in a single image, this technique can take several hours using current computer systems. Obviously, such a long processing time is inadequate for real-time or near-real-time image processing.

Monte-Carlo techniques are also problematic in that they do not converge for pure scattering media. This may be unacceptable when trying to model multiple scattering of certain media.

Another technique for modeling the impact of particles in the atmosphere on light is to use the plane parallel model. This model has been used in fields such as atmospheric optics and astronomy in which the medium being observed (e.g., the atmosphere around the earth) is illuminated by a distant light source such as the sun or moon. The plane parallel technique is problematic, however, in that it assumes that the light source is entering the medium from an infinitely far away distance, which is not the case when modeling the impact of an atmosphere on the appearance of a light source that is inside that atmosphere.

Accordingly, other techniques for modeling the multiple scattering of light from encompassed light sources and for using those models are desired.

SUMMARY OF THE INVENTION

The present invention provides systems and methods for modeling the impact of a medium on the appearance of an encompassed light sources using a Legendre polynomial series solution to a Radiative Transfer Equation for Spherical Media (RTE-SM) called an Atmospheric Point Spread Function (APSF). Using this APSF, it is possible to determine characteristics of the medium causing the multiple scattering of the light from the encompassed light source. For example, by observing a street light in bad weather at night, using the APSF, it is possible to determine whether the bad weather is haze, mist, fog, or rain. Similarly, the APSF may be used to estimate the size of particles in a liquid. It is also possible using the APSF to remove and/or add an effect of the medium on a light source captured in an image.

In accordance with an embodiment of the invention, a system features an image acquisition device that captures an image of a light source encompassed in a medium and a computer that receives the image from the image acquisition device, identifies the light source in the image, models the multiple scattering of light from the light source in the medium using a RTE-SM, and determines one or more properties of the medium using the RTE-SM.

In accordance with another embodiment of the invention, a system features a computer that receives an image, identifies a light source in the image, generates a model of multiple scattering of light from the light source in a medium in the image using a RTE-SM, and alters the image based upon the model.

In accordance with another embodiment of the invention, a method features capturing an image of a light source, identifying the light source in the image, modeling the multiple scattering of light from the light source in the medium using a RTE-SM, and determining one or more properties of the medium using the RTE-SM.

In accordance with another embodiment of the invention, a method features receiving an image, identifying a light source in the image, generating a model of multiple scattering of light from the light source in a medium using a RTE-SM, and altering the image based upon the model.

In accordance with another embodiment of the invention, a method of monitoring weather conditions features locating an image acquisition device in a location suitable for capturing images of multiple light sources, sequentially aiming the direction of the image acquisition device at each of the multiple light sources, capturing an image of each of the multiple light sources, identifying the light source in each of the images, modeling multiple scattering of light from the light source using a RTE-SM, and determining at least one of the forwarding scattering parameter, the optical thickness, the visibility of the atmosphere around the light sources using the RTE-SM.

In accordance with another embodiment of the invention, a method of monitoring weather conditions features locating a first image acquisition device in a first location suitable for capturing images of a first light source, locating a second image acquisition device in a second location suitable for capturing images of a second light source, capturing an image of each of the first light source and the second light source, identifying the light source in each of the images, modeling multiple scattering of light from the each light source using a Radiative Transfer Equation for Spherical Media, and determining at least one of the forward scattering parameter, the optical thickness, the visibility of the area using the Radiative Transfer Equation for Spherical Media.

In accordance with another embodiment of the invention, a method of monitoring weather conditions features locating an image acquisition device in a location suitable for capturing images of a light source, capturing multiple images of the light source, averaging the images to produce an averaged image, identifying the light source in the averaged image, modeling multiple scattering of light from the light source as captured in the averaged image using a Radiative Transfer Equation for Spherical Media, and determining at least one of the forward scattering parameter, the optical thickness, the visibility of an area using the Radiative Transfer Equation for Spherical Media.

DESCRIPTION OF PARTICULAR EMBODIMENTS OF THE INVENTION

Figure 1:
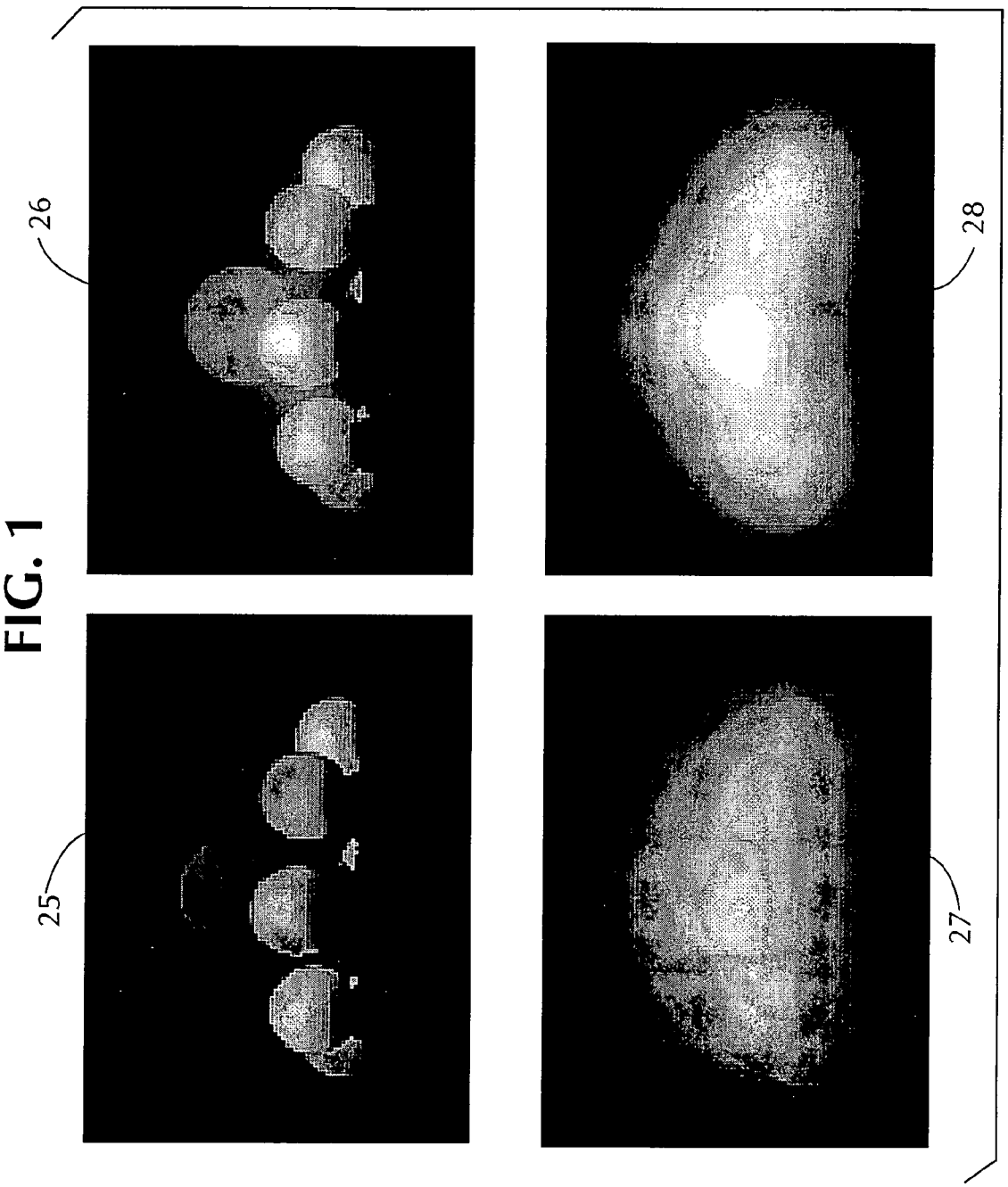
FIG. 1 shows four images illustrating multiple scattering of light from a light source.

Turning first to FIG. 1, an example of a street lamp in four different atmospheric conditions is illustrated in images 25, 26, 27, and 28. As can be seen, in the first image 25, no glow surrounds the individual globes of the street lamp. This is the case because the weather as shown in the image is clear. In image 26, however, it is apparent that the street lamp is now encompassed by mild fog and a slight glow appears around the individual globes of the lamp. Next, in image 27, the individual globes of the street lamp are all but obscured by the dense mist that now encompasses the street lamp. Finally, in image 28, the individual globes of the street lamp cannot be discerned because of the highly dense haze encompassing the street lamp. The glows surrounding the lamp in images 26, 27, and 28 are the result of multiple scattering of the light rays that are exiting the individual globes of the lamp.

Figure 2:
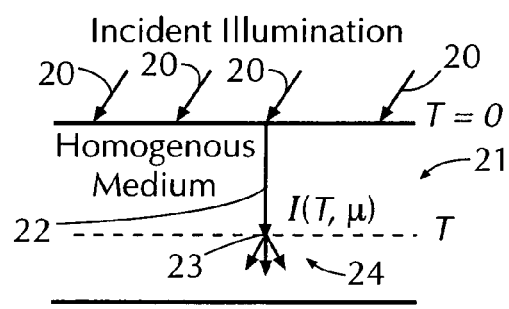
FIG. 2 shows an illustration of a prior art approach to modeling light scattering.
Figure 3:
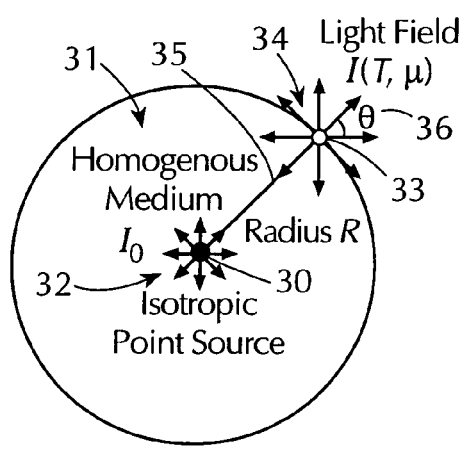
FIG. 3 shows an illustration of an embodiment of an approach to spherical modeling in accordance with the present invention.

Referring to FIGS. 2 and 3, two different scenarios for light from a light source impacting a medium are illustrated. First, as shown in FIG. 2, a light source 20 impacts a homogenous medium 21 from an infinite distance. Light rays 22 from source 20 travel through medium 21 and scatter at point 23 in various directions as indicated by scattered light rays 24. Because the light rays from source 20 impact the plane of medium 21 from an infinite distance in a parallel fashion, this is referred to as a plane parallel medium. Such a medium is not a good representation of an isotropic light source within an encompassing medium (like the street lamp in FIG. 1) because, unlike the parallel impact of the rays from the external light source in the plane parallel medium, light rays from a light source within an encompassing medium enter the medium radially from the light source.

A better representation is the spherical medium illustrated in FIG. 3. As shown, a light source 30 is encompassed by a homogenous medium 31. Light source 30 might be a street lamp within a medium 31 such as dense fog. Light rays 32 from source 30 radiate isotropically from source 30. Some of the rays 32 reach a "pin hole camera" 33 at a radius 35 from source 30 and then impact a surface within the camera at different points 34 and at different angles θ, 36, relative to and normal to the camera's pin hole. In the spherical medium representation, it is assumed that the medium is homogeneous and infinite in extent.

Figure 4:
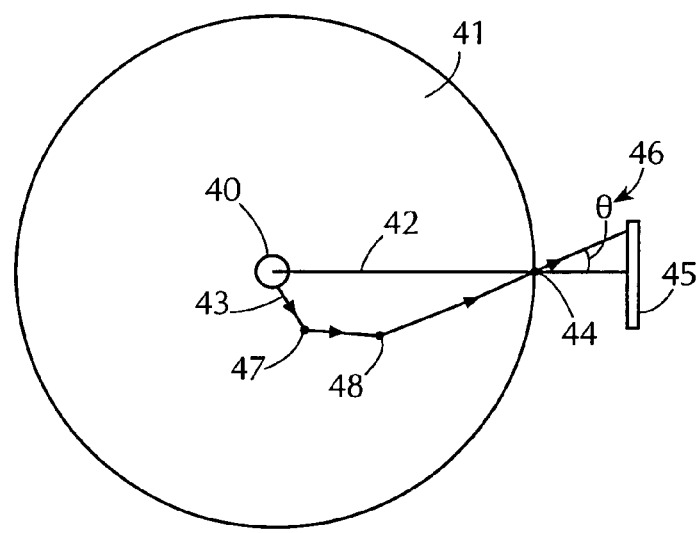
FIG. 4 shows another illustration of an embodiment of an approach to spherical modeling in accordance with the present invention.

An alternate view of the spherical medium 31 shown in FIG. 3 is illustrated in FIG. 4. As can be seen, a medium 41 encompasses a light source 40 that is outputting a light ray 43. Light ray 43 scatters at points (particles) 47 and 48 and passes through pin hole 44 and onto camera plane 45. The angle between the last leg of ray 43 hitting plane 45 and the straight line 42 between light source 40 and plane 45 is represented by angle θ, 46. Other rays that reach plane 45 from source 40 through pin hole 44 may hit plane 45 at other angles also represented by angle θ.

Figure 5:
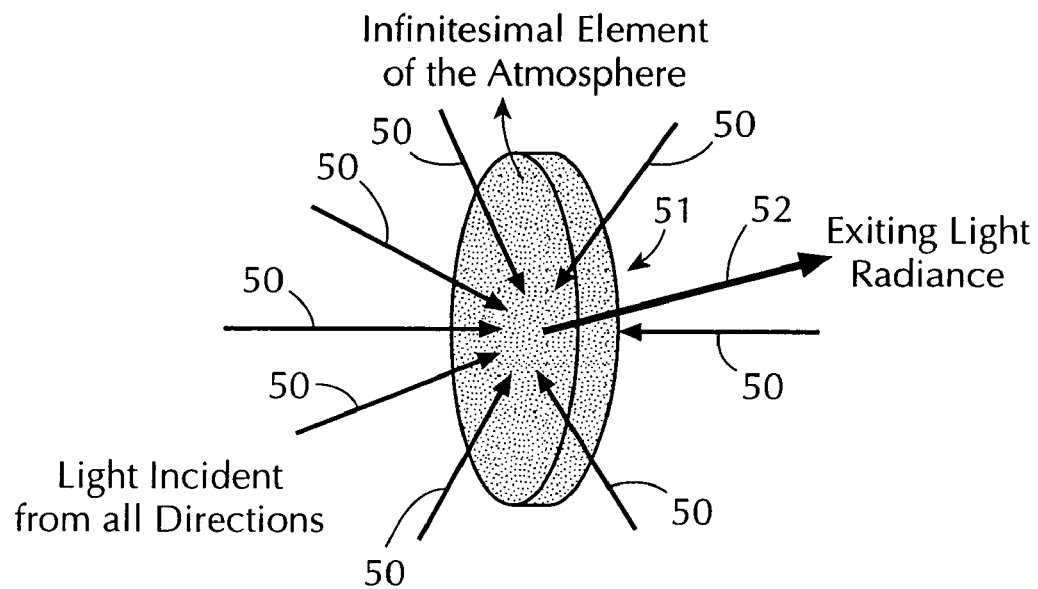
FIG. 5 shows an illustration of light incident on and exiting from an infinitesimal element of the atmosphere in accordance with an embodiment of the present invention.

Generally speaking, light scattering in a spherical medium, such as the earth's atmosphere, water solutions, blood, tissue, smoke, milk, etc., can by modeled by the physics-based theory of radiative transfer. As illustrated in FIG. 5, the key idea in this approach is to investigate the difference between light 50 incident on and light 52 exiting from an infinitesimal volume 51 of the medium. The change in flux through such volume 51 can then be given by an integro-differentiation equation called a Radiative Transfer Equation for Spherical Media (RTE-SM).

More specifically, a solution to the RTE-SM can be determined as follows. First, the directional distribution of light incident on a particle, called the scattering or phase function of the particle (P(cos α)), must be considered. For most atmospheric conditions, this phase function is known to be symmetric about the direction of incident light. Thus, the phase function depends only on the angle α between the directions of incident and scattered radiation. The cosine of this angle is determined as:

$$\cos \alpha = \mu\mu' + \sqrt{(1-\mu^2)(1-\mu'^2)}\cos(\phi-\phi')) \quad (1)$$

wherein:
θ,φ is the direction of the scattered radiance;
θ',φ' is the direction of the incident irradiance;
μ=cos θ; and
μ'=cos θ'.

Axially symmetric phase functions (both isotropic and anisotropic) can be expanded using Legendre polynomials $L_k$ as:

$$P(\cos\alpha) = \sum_{k=0}^{\infty} W_k L_k(\cos\alpha) \quad (2)$$

The exact shape of the phase function depends on the size of the scattering particles. For instance phase functions of small particles (e.g., air molecules) have a small peak in the direction of incidence. Isotropic and Rayleigh phase functions describe the scattering for air molecules. An Isotropic phase function that may be used in the present invention can be expressed as:

$$P(\cos \alpha) = W_0 \quad (3)$$

wherein:
$W_k=0$ for all k>=1.

A Rayleigh phase function that may be used in the present invention can be expressed as:

$$P(\cos\alpha) = \frac{3W_0}{4}(1+\cos^2\alpha) \quad (4)$$

wherein:
$W_1=0$;
$W_2=W_0/2$; and
$W_k=0$ for all k>=3.

Yet another phase function that may be used in the present invention can be expressed as:

$$P(\cos \alpha) = W_0(1+x \cos \alpha) \quad (5)$$

wherein:
−1<=x<=1;
$W_1=W_0 x$; and
$W_k=0$ for all k>=2.

Still another phase function that holds for particles of various sizes, that may be used in the present invention, and that is used herein for purposes of illustration is the Henyey-Greenstein phase function:

$$P(\cos \alpha) = 1 - q^2/(1+q^2-2q \cos \alpha)^{3/2} \quad (6)$$

wherein:
q is the forward scattering parameter and is between 0 (i.e., isotropic scattering) and 1 (i.e., anisotropic scattering—all scattering in forward direction); and
the coefficients of the Legendre polynomial expansion are:

$$W_k = W_0(2k+1)q^k \text{ for k>=1}.$$

Note that the $W_0$ coefficient is called the single scattering albedo, which is the fraction of flux scattered. When $W_0=1$, the medium is purely scattering, and if $W_0<1$, there is absorption.

Next, the Radiative Transfer Equation for Spherical Media (RTE-SM) for a spherically symmetric atmosphere may be written as:

$$\mu\frac{\partial I}{\partial T} + \frac{1-\mu^2}{T} = -I(T,\mu) + \frac{1}{4\pi}\int_0^{2\pi+1}\int_{-1} P(\cos\alpha)I(T,\mu')\partial\mu'\partial\phi' \quad (7)$$

Finally, by expanding the Henyey-Greenstein phase function in terms of Legendre polynomials, these equations can be solved as the Atmospheric Point Spread Function (APSF) (the derivation for this equation is presented at the end of this Detailed Description):

$$I(T, \mu) = \sum_{m=0}^{\infty} (g_m(T) + g_{m+1}(T))L_m(\mu) \qquad (8)$$

wherein:

I(T,μ) is the intensity of light;

$L_m(\mu)$ is the Legendre polynomial of order m, $$L_m(\mu) = \frac{1}{2^m m!} \frac{\partial^m}{\partial \mu^m} (\mu^2 - 1)^m;$$

$$g_m(T) = I_0 e^{-\beta_m T - \alpha_m \log T};$$

$$\alpha_m = m + 1;$$

$$\beta m = \left(\frac{2m+1}{m}\right)\left(1 - \frac{W_{m-1}}{2m-1}\right) = \left(\frac{2m+1}{m}\right)(1 - q^{m-1});$$

q is the forward scattering parameter;

T is the optical thickness of the medium, $$T = \sigma R \approx \frac{3.912}{V} R;$$

σ is the extinction coefficient which denotes the fraction of flux lost due to scattering within a unit volume of the medium;

V is the visibility of the medium;

R is the distance from the light source to the camera's pin hole; and

μ=cos θ.

In these equations, the function $g_m(T)$ captures the attenuation of light in the medium, whereas the Legendre polynomial $L_m(\mu)$ explains the angular spread of the brightness observed due to multiple scattering. This model is valid for both isotropic (i.e., q=0) as well as anisotropic (i.e., 0<q<=1) scattering, and thus describes glows under several weather conditions. The series solution in equation (8) does not converge for T<=1. Nevertheless, multiple scattering is very small for small optical thicknesses (i.e., when T<=1) and thus glows are not seen.

Figure 6:
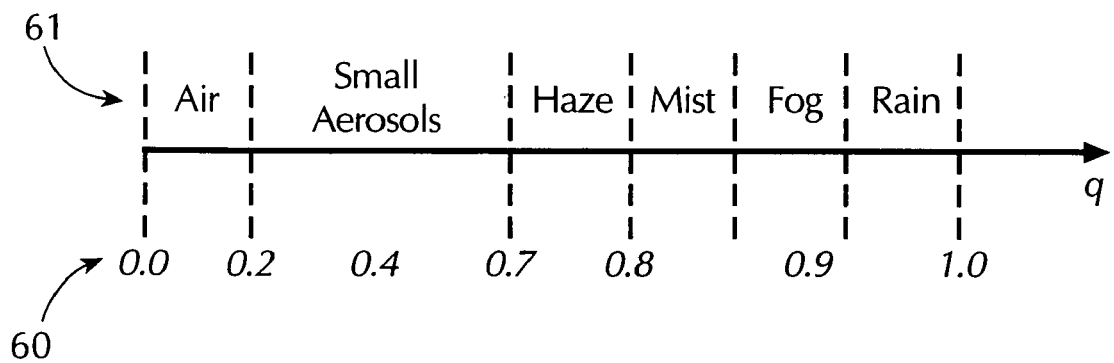
FIG. 6 shows an illustration of classifications of different ranges of forward scattering parameters q in accordance with an embodiment of the present invention.

As illustrated in FIG. 6, in an embodiment in which the APSF is being used to model multiple scattering in the earth's atmosphere, different values of q, 60, can be used to represent different weather conditions 61. For example, values of q, 60, ranging from 0.0 to 0.2 may represent "air," values ranging from 0.2 to 0.7 may represent "small aerosols," values ranging from 0.7 to 0.8 may represent "haze," values ranging from 0.8 to 0.9 may represent "mist" or "fog," and values ranging from 0.9 to 1.0 may represent "rain." Thus, as can be seen, q is an indicator of the size of the particles causing the multiple scattering. It is apparent that the boundary values in this example, e.g., 0.7, are approximate and do not strongly indicate which of the two bordering weather conditions is present.

Figure 7:
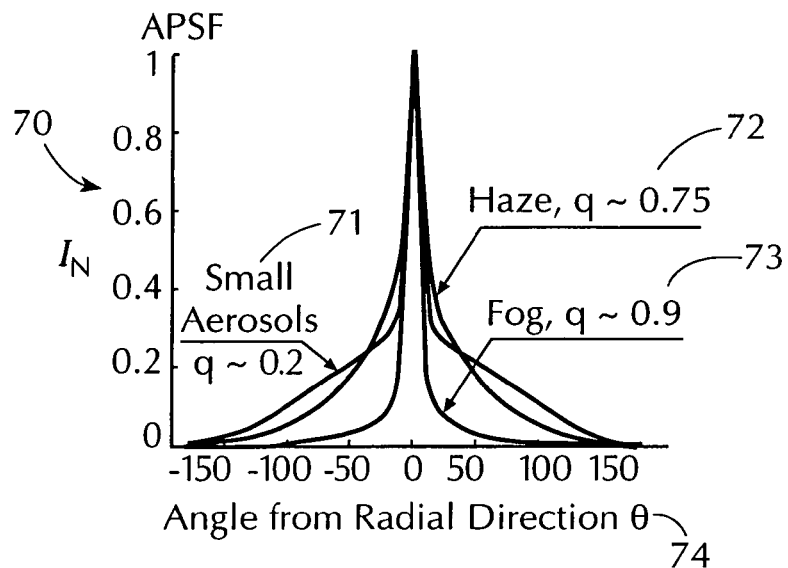
FIG. 7 shows a graph of an Atmospheric Point Spread Function (APSF) in accordance with one embodiment of the present invention.
Figure 8:
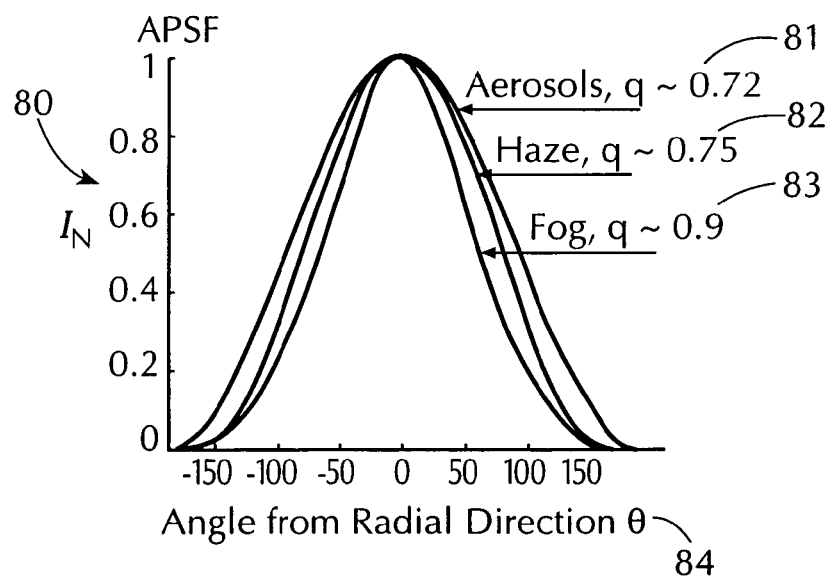
FIG. 8 shows another graph of an APSF in accordance with one embodiment of the present invention.

Turning to FIGS. 7 and 8, illustrations of the results of the APSF are shown for two different extinction coefficients, σ. These results are normalized so that the value of intensity I (on the y-axes 70 and 80) ranges from 0 to 1. On the x-axes 74 and 84, the values represented are the angles of θ, 46 (FIG. 4), from the camera's pin hole 44 (FIG. 4) relative to the camera's plane 45 (FIG. 4) for the corresponding values of I. As can be seen in FIG. 7, the curves 71, 72, and 73 represent the APSF for the spherical model for medium when containing "small aerosols," "haze," and "fog," respectively. As also shown, the values for q for these three curves are approximately 0.2, 0.75, and 0.9, respectively. Turning to FIG. 8, it can be seen that curves 81, 82, and 83 similarly represent the APSF for the spherical model for a medium when containing "aerosols," "haze," and "fog," respectively. Also similarly, the values for q for these three curves are approximately 0.2, 0.75, and 0.9, respectively.

As can be seen from these curves, larger particles (such as fog particles) result in greater forward scattering, and thus will result in narrower or more pointed APSF curves. As can also be seen from the curves, curves 81, 82, and 83 in FIG. 8 are wider than the corresponding curves 71, 72, and 73 in FIG. 7. This is because the extinction coefficient (σ) (and hence the optical thickness (T)) is much greater in FIG. 8 than in FIG. 7 as a result of the atmosphere in FIG. 8 being much denser than that in FIG. 7.

Figure 9:
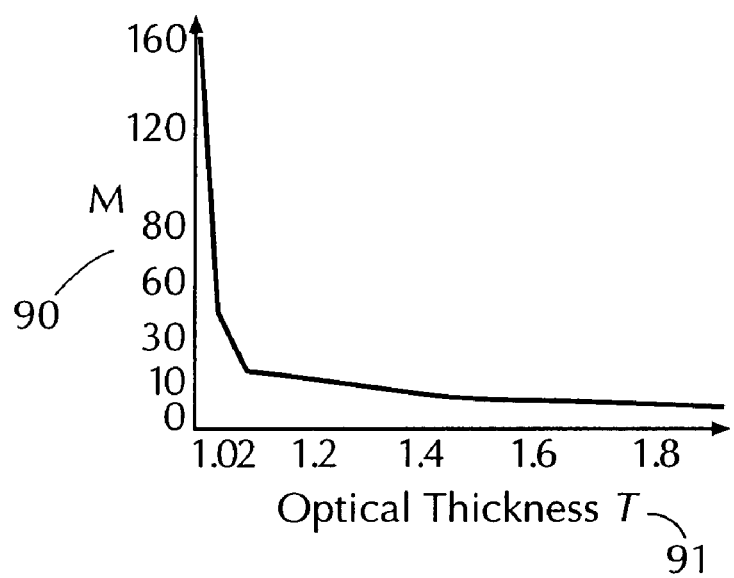
FIG. 9 shows a graph of the coefficient term m value versus optical thickness T in accordance with one embodiment of the present invention.

Before equation (8) can be solved, it is necessary to determine how many coefficients m to use. As can be seen in FIG. 9, the number of coefficient terms m, 90, to use is a function of the optical thickness T, 91, of the medium. Because T may not be known when solving the APSF, a value of m greater than 200 should be sufficient to solve the APSF. In the event that too few coefficient terms m are used, ringing will appear on the APSF curve such as that shown in curve 100 of FIG. 10 at points 102. Note that in FIG. 10, when m=200 in curve 101, no ringing is apparent.

Figure 10:
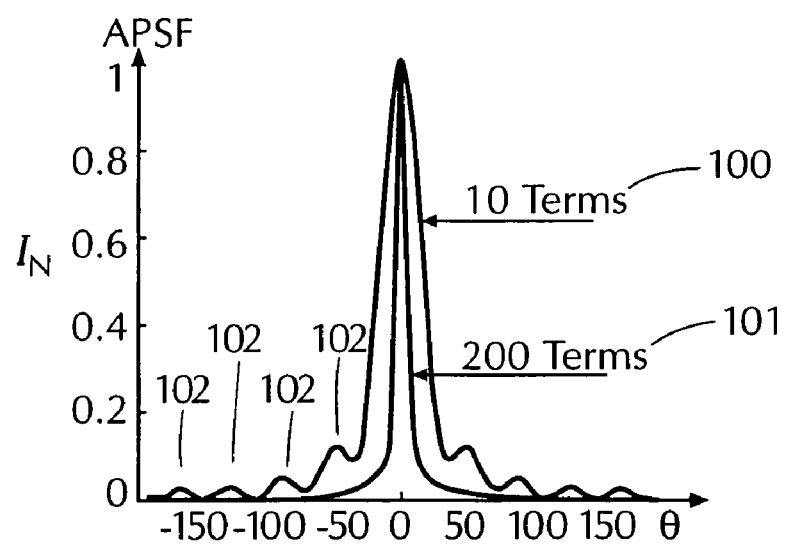
FIG. 10 shows a graph of an APSF in which ringing is present because not enough coefficient terms m were used in calculating the APSF in accordance with one embodiment of the present invention.

Using equation (8), it is now possible to determine the weather conditions and visibility from an image or to alter the glow (if any) in an image based upon desired weather conditions and visibility. In order to determine the weather conditions, the process of FIG. 11 may be used. As shown, at step 102, an image may be captured using any suitable image acquisition device, for example a camera. Next, at step 103, the image is transferred to a suitable computer. The process then determines the values of $I_0$ (the intensity of the source), R (the range from the source to the camera), and m (the number of coefficient terms to use) at step 104. In order to determine $I_0$ when $I_0$ is captured by more than one pixel in the CCD of the camera, it may be necessary to treat $I_0$ as a light source with an atypical shape or size, as discussed below in connection with FIG. 15, and use a thresholding technique to identify the shape function S of the source and then use the shape function to convolve the intensity values $I_0$. At step 105, the computer may then average the intensity values I captured by the camera along the radial contours of the image. In order to increase the signal-to-noise ratio of the image (e.g., when using an inexpensive camera as the image acquisition device), in some embodiments the average intensity values of intensity I and the value of source intensity $I_0$ may also be individually averaged over time. Next, using a suitable curve fitting algorithm, such as multidimensional unconstrained nonlinear minimization (i.e., Nelder-Mead search), the values of T and q can be calculated so that equation (8) approximates the curve provided by the measured values of I at step 106. These values of T and q can then be plugged into equation (8) to determine if any ringing exists in the resultant APSF curve as shown in FIG. 10. In the event that any ringing is present, step 108 may then be performed to increase the value of m, after which step 106 is repeated. Otherwise, if no ringing is present, the weather in the image may be looked-up from the determined value of q at step 109. The visibility may then be determined at step 110 based upon the values of T and R. Finally, at step 111, the data is output to the desired user or application.

Figure 11:
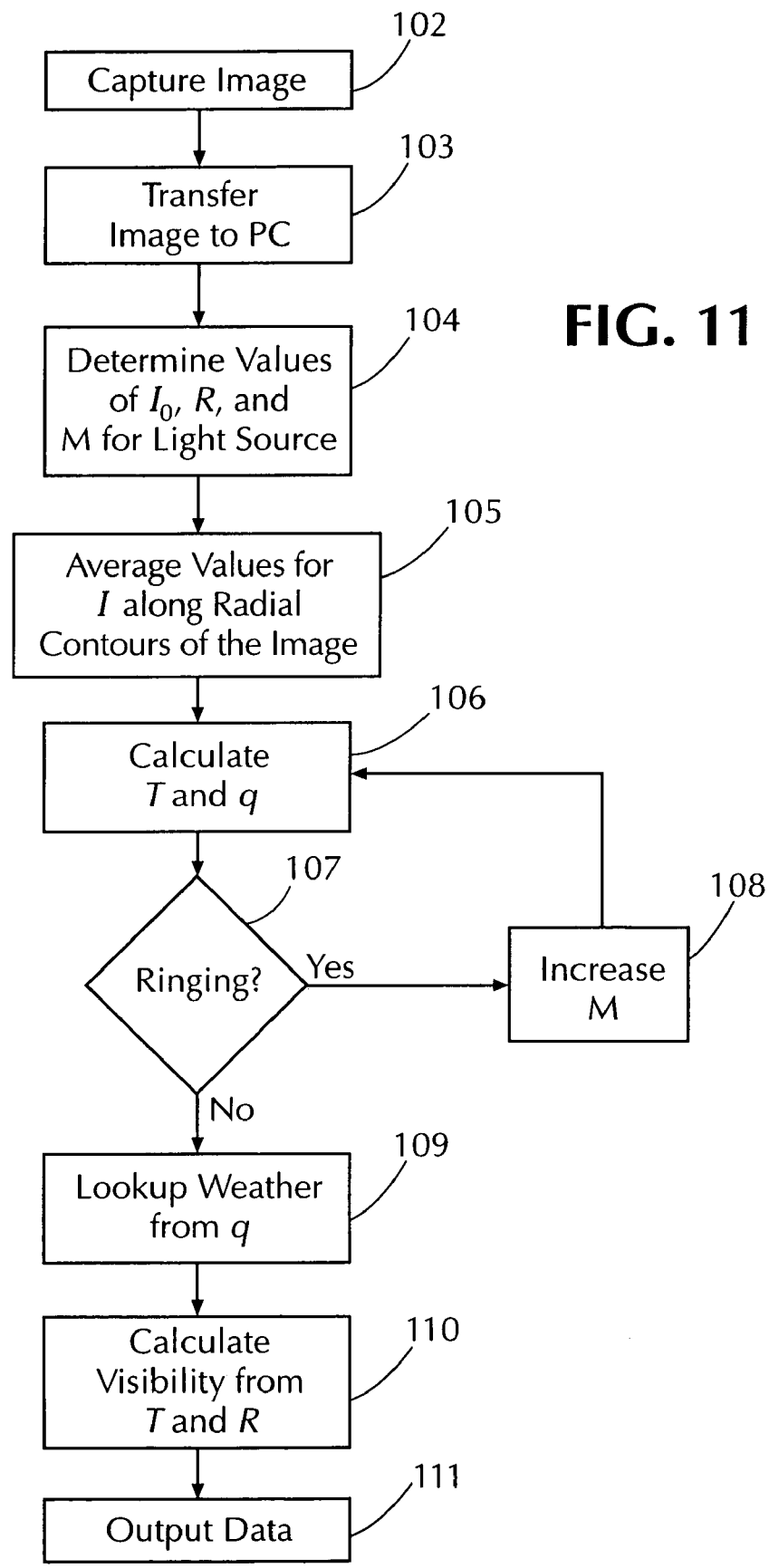
FIG. 11 shows a flowchart illustrating a process for calculating the forward scattering parameter q and the optical thickness T in accordance with one embodiment of the present invention.

Although the process in FIG. 11 used a known value of R to calculate values of T and q, it is possible to use known values of T to calculate values of R and q, and to use known values of q to calculate values of T and R in substantially the same manner.

Figure 12:
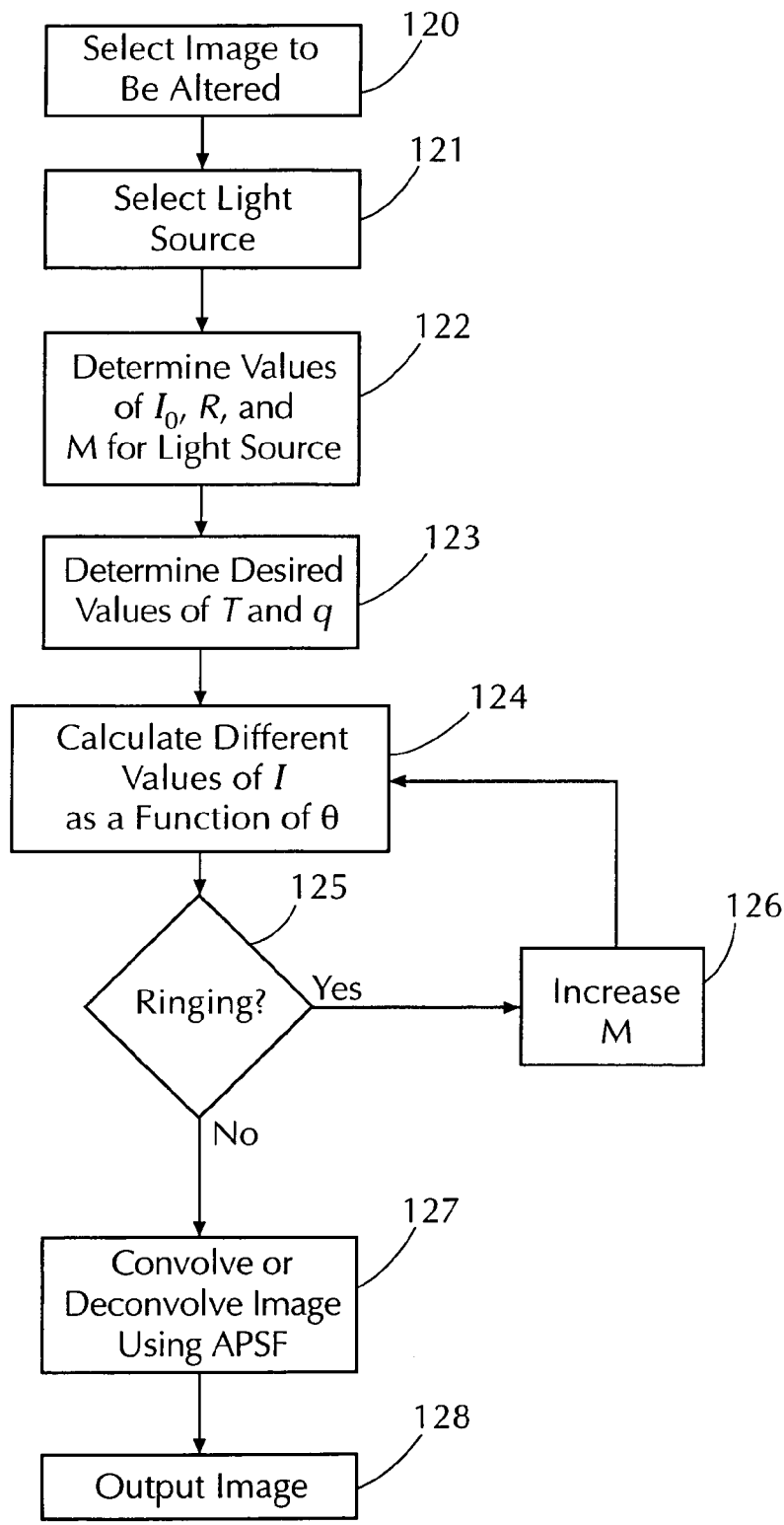
FIG. 12 shows a flowchart illustrating a process for altering an image in accordance with one embodiment of the present invention.

In order to alter glow (if any) in an image based upon desired weather conditions and visibility, the process in FIG. 12 may be performed. First, at step 120, the image to be altered may be selected. Next, at step 121, the light source in the image may be determined. The values of $I_0$ (the intensity of the light source in the image), R (the range to the light source in the image), and m (the number of coefficient terms to use) may be determined at step 122. In order to determine $I_0$ when $I_0$ is captured by more than one pixel in the CCD of the camera, it may be necessary to treat $I_0$ as a light source with an atypical shape or size, as discussed below in connection with FIG. 15, and use a thresholding technique to identify the shape function S of the source and then use the shape function to convolve the intensity values $I_0$. Next, at step 123, the desired values of T and q are determined. Using equation (8), the APSF is then determined at step 124. This determination provides the values of I for the different values of θ. At step 125, the process then determines if there is any ringing in the values of I as shown in FIG. 10. If ringing is present, the number of coefficient terms m is then increased at step 126 and step 124 repeated. Otherwise, if no ringing is present, the image is then convolved or deconvolved using the APSF at step 127 to add or remove a glow. Finally, at step 128, the image is output to the desired user or application.

In the event that the lens optics of the camera used in embodiments of the present invention has a small field of view (e.g., when using a zoom lens), intensities (I) from some directions may be cut-off. In such case, the glow surrounding the light source can be approximated by multiplying the intensity values at the outer edge of the glow by a constant attenuation factor ($e^{-T}/R^2$) and then using the product of that multiplication for all values of I.

Figure 13:
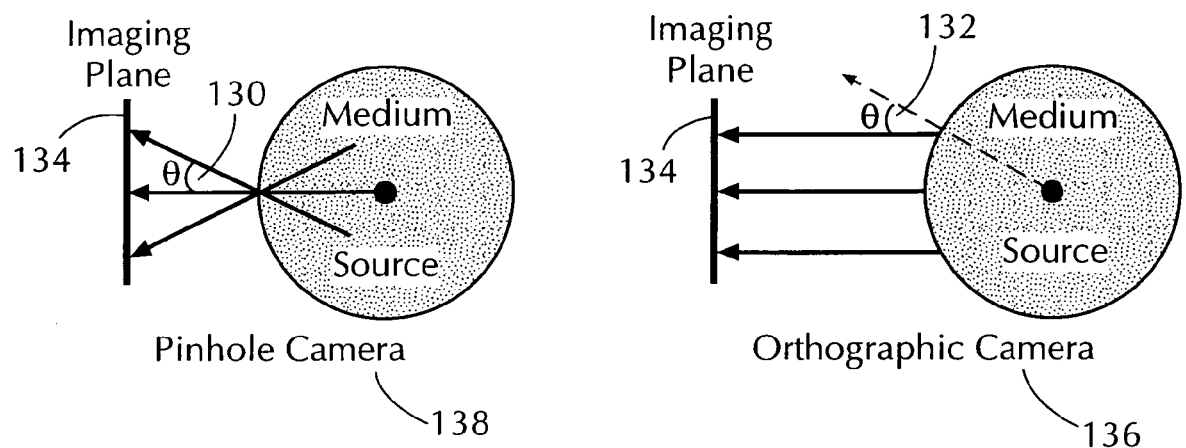
FIG. 13 shows an illustration of two possible arrangements of cameras and mediums being imaged in accordance with an embodiment of the present invention.
Figure 14:
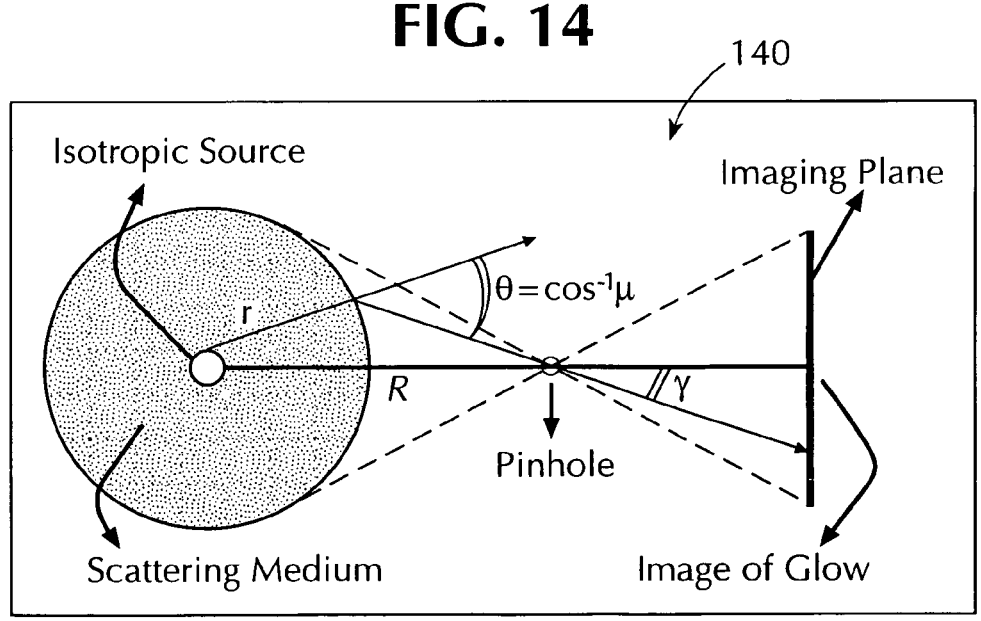
FIG. 14 shows an illustration of another possible arrangement of a camera and a medium being imaged in accordance with an embodiment of the present invention.

Alternate equations for the definition of µ may be necessary to take into account the geometry of any particular arrangement of camera and medium being imaged. For example, as illustrated in FIG. 13, when an orthographic camera 136 is used instead of a pin hole camera 138, angle θ in the equation µ=cos θ should be equal to angle 132 relative to the perpendicular of plane 130 rather than angle 134. As another example, as illustrated in FIG. 14, when a pin hole camera is used that is not within the medium such as in arrangement 140, the variable µ may be represented by the following:

$$\mu = \sqrt{1 - \frac{R^2}{r^2}\sin^2\gamma}$$

Figure 15:
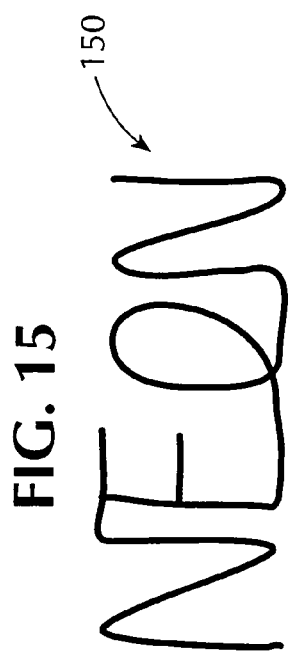
FIG. 15 shows an illustration of an atypical shape and size light source in accordance with one embodiment of the present invention.

In certain instances, it may be desirable to model a light source of an atypical shape or size, such as the neon sign 150 illustrated in FIG. 15. Such sources can be assumed to be made up of several isotropic source elements with varying radiant intensities $I_0(x,y)$. By the principle of superposition of light (it is assumed that the source elements are incoherent), the intensities due to different source elements can be added to yield the total intensity due to the light source. It is also assumed that the entire area of the light source is at the same depth from the observer and passes through the same atmosphere. The image of a light source of arbitrary shape and size may then be written as the following convolution:

$$I=(I_0S)*APSF$$

wherein:
S is a characteristic shape function that is constant over the extent of the light source (not including the glow).
Because APSF is rotationally symmetric, this two-dimensional convolution can be replaced by two one-dimensional convolutions in order to render the source more quickly.

In order to determine the shape function S, it may be necessary in certain cases to determine the shape function by performing thresholding or high-pass filtering on the corresponding area of the image. Another approach is to determine the APSF from a nearby first light source and then use that APSF to deconvolve the image of the second source and remove the glow around the second source. This may be advantageous where the shape of the first light source is simple, or it is likely to be easier to perform thresholding on that light source. For example, taking a first source and applying a simple thresholding function to the source may give a shape function $S_1$ for that source. Assuming that the radiant intensity of the first source is constant across the source, the APSF can then be recovered from the following function:

$$APSF=I*(I_0S_1)^{-1}$$

This normalized APSF can then be used to deconvolve the image of the second source and remove the glow around the second source using the following function:

$$S_2=I*(I_0APSF)^{-1}$$

With color images, it is necessary to calculate q and T separately for each of the three colors making up the images. In doing so, each value of I and $I_0$ should correspond to the appropriate color.

Figure 16:
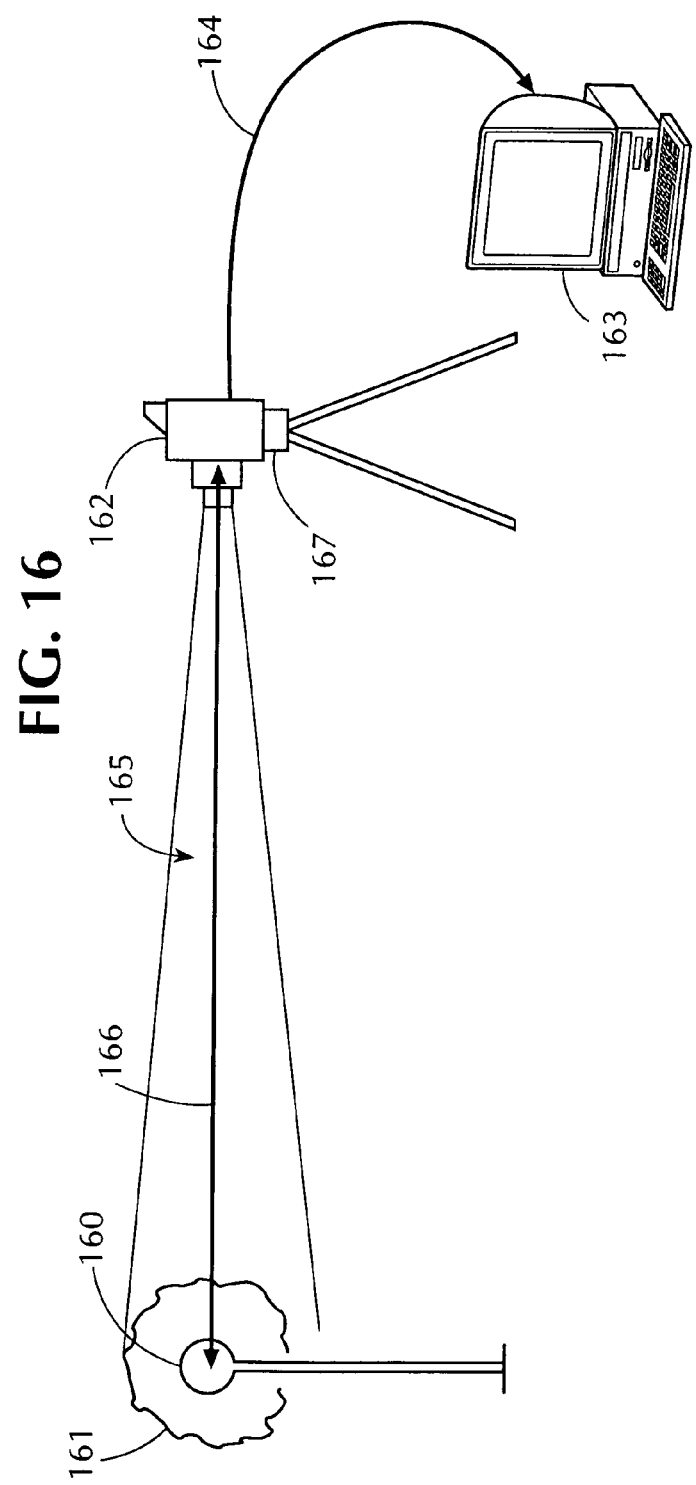
FIG. 16 shows a block diagram of equipment in one embodiment of the present invention.
Figure 17:
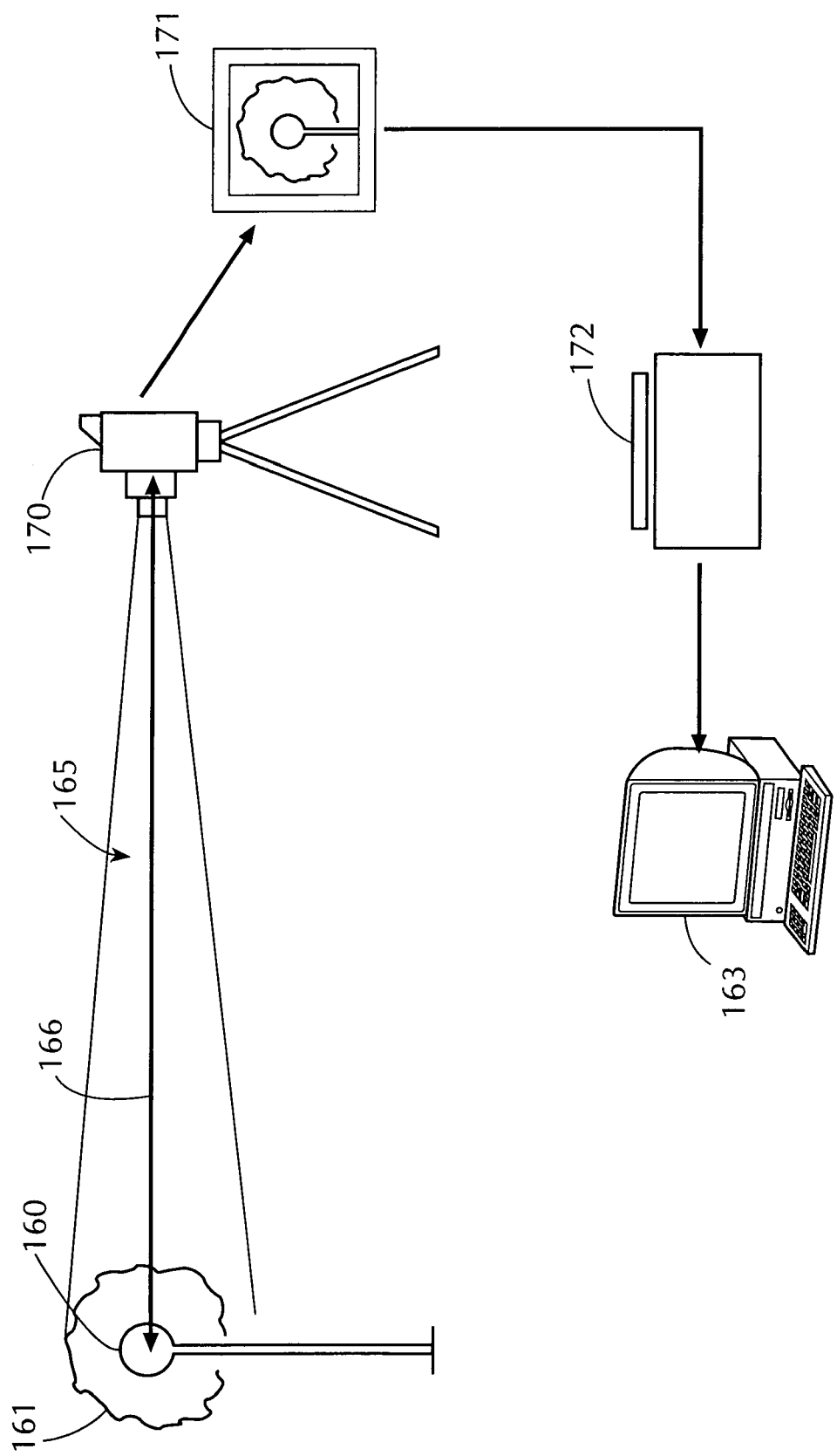
FIG. 17 shows a block diagram of equipment in another embodiment of the present invention.

Turning now to FIG. 16, one embodiment of equipment for implementing the present invention is shown. As can be seen, an image acquisition device 162 is used to capture an image of a lamp 160 possibly having a glow 161. The field of view of device 162 is represented by a field 165. The distance from device 162 to lamp 160 is represented by a line 166. Once an image is captured, the image may then be transferred to a computer 163 using a link 164. Device 162 may be any suitable image acquisition device, such as a Kodak DCS 760 camera or any other suitable camera, video camera, optical sensor, etc., that is radiometrically calibrated. The computer may be any suitable computer, such as a personal computer, a micro computer, a server, a workstation, a mainframe, a laptop, a PDA, a computer incorporated in a telephone (e.g., a cellular telephone), a computer in device 162 or another camera, etc. Link 164 may be any suitable link such as a USB interface (e.g., versions 1.0 or 2.0), IEEE 1394 interface, a serial link, or any other suitable link. An alternate embodiment is shown in FIG. 17. As illustrated, camera 170 may be a film or instant photography camera. An image from that camera may then be placed in any suitable scanner 172 for transferring the image into computer 163. In such an implementation, the aperture settings of camera 170 may need to be fixed to match a radiometric calibration of scanner 172.

In both of these embodiments it may be necessary to take into account the Optical Transfer Function (OTF) of any camera or scanner used in accordance with the invention. First, it may be desirable to check the camera or scanner to verify that the OTF of the camera or scanner does not affect the frequencies of the APSF. This can be accomplished by (i) plotting all possible frequencies of the APSF by taking the Fourier transform of $I(T,\mu)$ in equation (8) for all possible values of T (e.g., by selecting maximum R and V values and using the formula for T set forth above) and $\mu$, and (ii) measuring the OTF using resolution charts. If the OTF is high (e.g., close to 1) for the main frequencies of the APSF, then the lens is acceptable. Otherwise, it may be desirable to select a better lens. Second, it may be desirable to deconvolve the images taken with the camera or scanner using the camera's or scanner's OTF.

In accordance with the present invention, the equipment illustrated in FIGS. 16 and 17 may be configured at any suitable location and arranged so that a single image acquisition device that is controlled by a motor 167 is used to monitor many different locations. For example, at an airport, the image acquisition device may be located on the control tower so that it can be aimed at various lights throughout the grounds of the airport. The computer may then be configured to control the motor so that the image acquisition device is periodically directed at each of these lights, an image captured, and the processing in FIG. 11 performed to determine the values of T and q in each of the various directions. If the appropriate image acquisition device is selected, the lights may be miles away from the camera. Such an arrangement could also be used on highways or in any other suitable location.

Similarly, multiple image acquisition devices could be used and each could be focused on a unique one or set of light sources. The images captured by those devices could then be processed as described above.

Derivation of Equation (8)

In this section, the derivation of an analytic form for $I(T,\mu)$ is provided. First, generally speaking, the partial derivative I with respect to $\mu$ is eliminated by integrating the RTE-SM with respect to $\mu$ over the range $[-1,+1]$. Here, the partial derivative is eliminated by using exact integrals instead of approximating the integrals by linear summations.

More particularly, by integrating the phase function P over the azimuth angle $\phi'$, a function that does not depend on the azimuth angle can be defined as:

$$P^{(0)}(\mu, \mu') = \frac{1}{2\pi} \int_0^{2\pi} P(\cos\alpha) \partial\phi' \qquad (9)$$

where, $$\cos\alpha = \mu\mu' + \sqrt{(1-\mu^2)(1-\mu'^2)} \cos(\phi - \phi') \qquad (10)$$

and, $\mu = \cos\theta$ and $\mu' = \cos\theta'$. As we shall see, the use of $P^{(0)}$ simplifies the mathematics involved in modeling the multiple scattering around a point light source. Substituting into the following equation for an RTE-SM:

$$\mu\frac{\partial I}{\partial T} + \frac{1-\mu^2}{T}\frac{\partial I}{\partial \mu} = -I(T,\mu) + \frac{1}{4\pi} \int_0^{2\pi+1}\int_{-1} P(\mu,\phi;\mu',\phi')I(T,\mu')\partial\mu'\partial\phi' \qquad (11)$$

we get:

$$\mu\frac{\partial I}{\partial T} + \frac{1-\mu^2}{T}\frac{\partial I}{\partial \mu} = -I(T,\mu) + \frac{1}{2}\int_{-1}^{+1} P^{(0)}(\mu,\mu')I(T,\mu')\partial\mu'. \qquad (12)$$

A function $Q_m(\mu)$ for some $m>0$ is defined such that:

$$Lm(\mu) = -\frac{\partial((1-\mu^2)Q_m(\mu))}{\partial\mu} \Leftrightarrow Q_m(\mu) = \frac{L'_m(\mu)}{m(m+1)} \qquad (13)$$

Consider the integral:

$$\int_{-1}^{+1}(1-\mu^2)Q_m\left(\frac{\partial I}{\partial \mu}\right)\partial\mu \qquad (14)$$

Integrating by parts and using (13), it has been shown that the partial derivative with respect to $\mu$ can be eliminated:

$$\int_{-1}^{+1}(1-\mu^2)Q_m\left(\frac{\partial I}{\partial \mu}\right)\partial\mu = \int_{-1}^{+1} I(T,\mu)L_m\partial\mu. \qquad (15)$$

When there is no confusion, the parameters $\mu$ and T can be dropped for brevity. Multiplying (12) by $Q_m$ and integrating with respect to $\mu$ over $[-1,+1]$, provides:

$$\int_{-1}^{+1}\mu Q_m\frac{\partial I}{\partial T}\partial\mu + \int_{-1}^{+1}\frac{1-\mu^2}{T}Q_m\frac{\partial I}{\partial \mu}\partial\mu = \qquad (16)$$
$$-\int_{-1}^{+1}Q_m I\partial\mu + \frac{1}{2}\int_{-1}^{+1}Q_m\partial\mu\int_{-1}^{+1} P^{(0)}(\mu,\mu')I(T,\mu')\partial\mu'.$$

Substituting equation (15), the RTE can be written as:

$$\int_{-1}^{+1}\mu Q_m\frac{\partial I}{\partial T}\partial\mu + \frac{1}{T}\int_{-1}^{+1} L_m I\partial\mu = \qquad (17)$$
$$-\int_{-1}^{+1}Q_m I\partial\mu + \frac{1}{2}\int_{-1}^{+1}Q_m(\mu)\partial\mu\int_{-1}^{+1} P^{(0)}(\mu,\mu')I(T,\mu')\partial\mu'.$$

Thus the partial derivative with respect to $\mu$ is eliminated from the RTE-SM leaving only the derivative with respect to the optical thickness T.

Next, it is assumed that a solution $I_m(T,\mu)$ to (17) is a product of two functions—$g(T)$ depending only on the optical thickness T, and $f(\mu)$ expressing the angular dependence. Mathematically, this is represented as:

$$I_m(T,\mu) = g_m(T)f_m(\mu) \qquad (18)$$

Substituting into (17), provides:

$$g'_m\int_{-1}^{+1}\mu Q_m f_m\partial\mu + \frac{g_m}{T}\int_{-1}^{+1} L_m f_m\partial\mu + g_m\int_{-1}^{+1} Q_m f_m\partial\mu - \qquad (19)$$

-continued
$$\frac{g_m}{2}\int_{-1}^{+1} Q_m \partial \mu \int_{-1}^{+1} P^{(0)}(\mu, \mu')f_m(\mu')\partial \mu' = 0$$

Since the RTE-SM is spherically symmetric (does not depend on the azimuth angle φ), a Legendre polynomial expansion (and not a spherical harmonic expansion) of I is possible. Therefore, suppose $$f_m(\mu) = L_{m-1} + L_m \quad (20)$$

for some m>0. As shall be shown, the above form is key to get a non-trivial solution to the RTE-SM ensuring none of the terms of the RTE-SM go to zero. Since the phase function P is symmetric about the direction of incident light, P can be expanded using Legendre polynomials as $$P(\cos\alpha) = \sum_{k=0}^{\infty} W_k L_k(\cos\alpha) \quad (21)$$

Then, by using (10), and the following identity:

$$L_k(\cos\Theta) = L_k(\mu)L_k(\mu') + 2\sum_{n=1}^{k} L_k^n(\mu)L_k^n(\mu')\cos n(\phi - \phi') \quad (22)$$

the following is provided:

$$P^{(0)}(\mu, \mu') = \sum_{k=0}^{\infty} W_k L_k(\mu) L_k(\mu') \quad (23)$$

Similarly $L'_k(\mu)$ and $\mu L'_k(\mu)$ can be expanded using a Legendre polynomial series:

$$L'_k(\mu)=(2k-1)L_{k-1}(\mu)+(2k-5)L_{k-3}(\mu)+\ldots \quad \mu L'_k(\mu)=kL_k(\mu)+(2k-3)L_{k-2}(\mu)+\ldots \quad (24)$$

Substituting equations (13), (20), (23), and (24) into equation (19) and simplifying each term using the orthogonality of Legendre polynomials:

$$\int_{-1}^{+1} L_i L_j \partial \mu = \frac{2}{2n+1} \text{ if } i = j = n;$$

$$\int_{-1}^{+1} L_i L_j \partial \mu = 0 \text{ otherwise;}$$

The above property can be used to greatly simplify the mathematics as detailed below.

Term 1 in equation (19):

$$g'_m \int_{-1}^{+1} \mu Q_m f_m \partial \mu = \frac{g'_m}{m(m+1)} \int_{-1}^{+1} \{\mu L'_m\}(L_{m-1} + L_m)\partial \mu \quad (25)$$

$$= \frac{g'_m}{m(m+1)} \int_{-1}^{+1} \{mL_m + (2m-3)L_{m-2} + \ldots\}(L_{m-1} + L_m)\partial \mu$$

$$= \frac{g'_m}{m(m+1)} \int_{-1}^{+1} \{mL_m\}(L_m)\partial \mu$$

$$= g'_m\left(\frac{2}{(m+1)(2m+1)}\right)$$

Term 2 in equation (19):

$$\frac{g_m}{T}\int_{-1}^{+1} L_m f_m \partial \mu = \frac{g_m}{T}\int_{-1}^{+1} L_m(L_{m-1} + L_m)\partial \mu = \frac{g_m}{T}\left(\frac{2}{2m+1}\right) \quad (26)$$

Term 3 in equation (19):

$$g_m \int_{-1}^{+1} Q_m f_m \partial \mu = \frac{g_m}{m(m+1)} \int_{-1}^{+1} \{L'_m\}(L_{m-1} + L_m)\partial \mu \quad (27)$$

$$= \frac{g_m}{m(m+1)} \int_{-1}^{+1} \{(2m-1)L_{m-1} + \ldots\}(L_{m-1} + L_m)\partial \mu$$

$$= \frac{2g_m}{m(m+1)}$$

Term 4 in equation (19):

$$\frac{g_m}{2}\int_{-1}^{+1} Q_m \partial \mu \int_{-1}^{+1} P^{(0)}(\mu, \mu')f_m(\mu')\partial \mu' = \frac{g_m}{2m(m+1)} \quad (28)$$

$$\int_{-1}^{+1} L'_m(\mu)\partial \mu \int_{-1}^{+1} \left(\sum_k W_k L_k(\mu)L_k(\mu')\right)(L_{m-1}(\mu') + L_m(\mu'))\partial \mu =$$

$$\frac{g_m}{2m(m+1)}\int_{-1}^{+1} L'_m(\mu)\left(\frac{2W_m}{2m+1}L_m(\mu) + \frac{2W_{m-1}}{2m-1}L_{m-1}(\mu)\right)\partial \mu =$$

$$\frac{g_m}{2m(m+1)}\int_{-1}^{+1} \{(2m-1)L_{m-1}(\mu) + \ldots\}$$

$$\left(\frac{2W_{m-1}}{2m-1}L_m(\mu) + \frac{2W_{m-1}}{2m-1}L_{m-1}(\mu)\right)\partial \mu =$$

$$\frac{g_m}{2m(m+1)}\left(\frac{2W_{m-1}}{2m-1}\right)(2m-1)\frac{2}{2m-1} = \frac{2g_m}{m(m+1)}\left(\frac{W_{m-1}}{2m-1}\right)$$

The fact that P(0) can be expressed as products of Legendre polynomials is clearly a considerable advantage in simplifying the terms of equation (19). Substituting the 4 terms from equations (25), (26), (27), and (28) into equation (19), provides:

$$g'_m\left(\frac{2}{(m+1)(2m+1)}\right) + \frac{g_m}{T}\left(\frac{2}{2m+1}\right) + \quad (29)$$

$$\frac{2g_m}{m(m+1)} - \frac{2g_m}{m(m+1)}\left(\frac{W_{m-1}}{2m-1}\right) = 0$$

The above equation can be simplified and written in a concise manner as:

$$g'_m + \frac{g_m}{T}\alpha_m + g_m\beta_m = 0 \quad (30)$$

wherein,

-continued $$\alpha_m = m + 1$$

$$\beta_m = \left(\frac{2m+1}{m}\right)\left(1 - \frac{W_{m-1}}{2m-1}\right)$$

For the Henyey-Greenstein phase function:

$$\beta_m = \left(\frac{2m+1}{m}\right)(1 - q^{m-1})$$

The solution to (30) is:

$$g_m(T) = I_0 e^{-\beta_m T - \alpha_m \log T} \qquad (31)$$

where the constant integration $I_0$ is the radiant intensity of the point source. Note that the above equation automatically satisfies the boundary condition:

$$g_m(\infty) = 0$$

By multiplying the RTE-SM by $Q_m$ for m=1 . . . ∞, the individual solutions can be superposed to get the final solution:

$$I(T, \mu) = \sum_{m=1}^{\infty} c_m g_m(T)(L_{m-1}(\mu) + L_m(\mu)). \qquad (32)$$

The values for coefficients Cm=1 for all m, satisfy desired boundary conditions and they are shown to be accurate through real experiments as well as numerical Monte Carlo simulations.

It is apparent that many advantages may be provided in the various embodiments of the systems and methods of the present invention. For example, in certain embodiments, weather, visibility, and range information corresponding to a light source captured in an image can be quickly determined. As another example, in certain embodiments, images can be altered to add or remove the appearance of multiple scattering effects. As yet another example, in certain embodiments, the techniques disclosed can be used for medical imaging of blood, tissues, or any other suitable portion of a body. As still another example, in certain embodiments, the techniques disclosed can be used for underwater imaging. As a further example, in certain embodiments, the results of the present invention can be used to narrow the scope of the integral in a Monte-Carlo technique for modeling multiple scattering and thereby speed up that process. As a still further example, in certain embodiments, these techniques may be used for both absorbing and purely scattering media. As a yet further example, in certain embodiments, these techniques may be used to average the impact of multiple scattering over a long distance or a long time, and thereby minimize noise impacts. As a still further example, in certain embodiments, these techniques may be used as a first step before performing a more thorough Monte Carlo analysis of multiple scattering in the medium.

Persons skilled in the art will thus appreciate that the present invention can be practiced by other than the described embodiments, which are presented for purposes of illustration and not of limitation, and that the present invention is limited only by the claims that follow.

What is claimed is:

1. A system for indicating a property of a medium, comprising:
   an image acquisition device that captures an image of a light source encompassed in the medium; and
   a computer that receives the image from the image acquisition device, identifies the light source in the image, models multiple scattering of light from the light source in the medium using a Radiative Transfer Equation for Spherical Media, and determines the property of the medium using the Radiative Transfer Equation for Spherical Media.

2. The system of claim 1, wherein the medium is the earth's atmosphere.

3. The system of claim 2, wherein, in determining the property of the medium, the computer determines whether particles surrounding the light source are one of aerosols, haze, mist, rain, and fog.

4. The system of claim 1, wherein the medium is within a body.

5. The system of claim 1, wherein the medium is one of blood and tissue.

6. The system of claim 1, wherein the medium is a water solution.

7. The system of claim 1, wherein the computer models the multiple scattering of the light using a Legendre polynomial.

8. The system of claim 1, wherein the computer models the multiple scattering of the light using an axially symmetric phase function.

9. The system of claim 1, wherein the computer models the multiple scattering of the light using a Henyey-Greenstein phase function.

10. The system of claim 1, wherein the computer models the multiple scattering of the light without using a Monte-Carlo technique.

11. The system of claim 1, wherein, in determining the property of the medium, the computer determines the forward scattering parameter of the medium.

12. The system of claim 1, wherein, in determining the property of the medium, the computer determines the relative size of particles surrounding the light source.

13. The system of claim 1, wherein, in determining the property of the medium, the computer determines the range from the light source to the image acquisition device.

14. The system of claim 1, wherein, in determining the property of the medium, the computer determines the optical thickness of the medium.

15. The system of claim 1, wherein, in determining the property of the medium, the computer determines the visibility to the light source.

16. The system of claim 1, wherein the computer also determines whether enough coefficient terms are being used in solving the Radiative Transfer Equation for Spherical Media.

17. The system of claim 1, wherein the computer also averages different values of detected intensity of a glow of the light source along radial contours of the image.

18. A system for altering an image, comprising:
   a computer that receives the image containing a light source encompassed in a medium, identifies the light source in the image, generates a model of multiple scattering of light from the light source in the medium using a Radiative Transfer Equation for Spherical Media, and alters the image based upon the model.

19. The system of claim 18, wherein the medium is the earth's atmosphere.

20. The system of claim 18, wherein the medium is within a body.

21. The system of claim 18, wherein the medium is one of blood and tissue.

22. The system of claim 18, wherein the medium is a water solution.

23. The system of claim 18, wherein the computer generates the model using a Legendre polynomial.

24. The system of claim 18, wherein the computer generates the model using an axially symmetric phase function.

25. The system of claim 18, wherein the computer generates the model using a Henyey-Greenstein phase function.

26. The system of claim 18, wherein the computer generates the model without using a Monte-Carlo technique.

27. The system of claim 18, wherein, in altering the image based upon the model, the computer adds a multiple scattering effect to the image.

28. The system of claim 18, wherein, in altering the image based upon the model, the computer removes a multiple scattering effect from the image.

29. A method for indicating a property of a medium, comprising the steps of:
    capturing an image of a light source encompassed in the medium;
    identifying the light source in the image;
    modeling multiple scattering of light from the light source in the medium using a Radiative Transfer Equation for Spherical Media; and
    determining the property of the medium using the Radiative Transfer Equation for Spherical Media.

30. The method of claim 29, wherein the medium is the earth's atmosphere.

31. The method of claim 30, wherein the determining step comprises determining whether particles surrounding the light source are one of aerosols, haze, mist, rain, and fog.

32. The method of claim 29, wherein the medium is within a body.

33. The method of claim 29, wherein the medium is one of blood and tissue.

34. The method of claim 29, wherein the medium is water solution.

35. The method of claim 29, wherein the modeling step uses a Legendre polynomial.

36. The method of claim 29, wherein the modeling step uses an axially symmetric phase function.

37. The method of claim 29, wherein the modeling step uses a Henyey-Greenstein phase function.

38. The method of claim 29, wherein the modeling step does not use a Monte-Carlo technique.

39. The method of claim 29, wherein the determining step comprises determining the forward scattering parameter of the medium.

40. The method of claim 29, wherein the determining step comprises determining the relative size of particles surrounding the light source.

41. The method of claim 29, wherein the determining step comprises determining the range from the light source to the camera.

42. The method of claim 29, wherein the determining step comprises determining the optical thickness of the medium.

43. The method of claim 29, wherein the determining step comprises determining the visibility to the light source.

44. The method of claim 29, further comprising determining whether enough coefficient terms are being used in solving the Radiative Transfer Equation for Spherical Media.

45. The method of claim 29, further comprising averaging different values of detected intensity of a glow of the light source along radial contours of the image.

46. A method for altering an image, comprising the steps of:
    receiving the image;
    identifying a light source encompassed in a medium in the image;
    generating a model of multiple scattering of light from the light source in the medium using a Radiative Transfer Equation for Spherical Media; and
    altering the image based upon the model.

47. The method of claim 46, wherein the medium is the earth's atmosphere.

48. The method of claim 46, wherein the medium is within a body.

49. The method of claim 46, wherein the medium is one of blood and tissue.

50. The method of claim 46, wherein the medium is a water solution.

51. The method of claim 46, wherein the generating step uses a Legendre polynomial.

52. The method of claim 46, wherein the generating step uses an axially symmetric phase function.

53. The method of claim 46, wherein the generating step uses a Henyey-Greenstein phase function.

54. The method of claim 46, wherein the generating step does not use a Monte-Carlo technique.

55. The method of claim 46, wherein the altering step adds a multiple scattering effect to the image.

56. The method of claim 46, wherein the altering step removes a multiple scattering effect from the image.

57. A method of monitoring weather conditions in an area, comprising the steps of:
    locating an image acquisition device in a location suitable for capturing images of multiple light sources encompassed in the area;
    sequentially aiming the direction of the image acquisition device at each of the multiple light sources;
    capturing an image of each of the multiple light sources; identifying the light source in each of the images;
    modeling multiple scattering of light from the light source using a Radiative Transfer Equation for Spherical Media; and
    determining at least one of the forward scattering parameter, the optical thickness, the visibility of area using the Radiative Transfer Equation for Spherical Media.

58. The method of claim 57, wherein the area is an airport.

59. The method of claim 57, wherein the area is a highway.

60. A method of monitoring weather conditions in an area, comprising the steps of:
    locating a first image acquisition device in a first location suitable for capturing images of a first light source encompassed in the area;
    locating a second image acquisition device in a second location suitable for capturing images of a second light source encompassed in the area;
    capturing an image of each of the first light source and the second light source; identifying the light source in each of the images;

modeling multiple scattering of light from each light source using a Radiative Transfer Equation for Spherical Media; and determining at least one of the forward scattering parameter, the optical thickness, the visibility of the area using the Radiative Transfer Equation for Spherical Media.

61. The method of claim 60, wherein the area is an airport.

62. The method of claim 60, wherein the area is a highway.

63. A method of monitoring weather conditions in an area, comprising the steps of:

locating an image acquisition device in a location suitable for capturing images of a light source encompassed in the area;

capturing multiple images of the light source;

averaging the images to produce an averaged image; identifying the light source in the averaged image;

modeling multiple scattering of light from the light source as captured in the averaged image using a Radiative Transfer Equation for Spherical Media; and determining at least one of the forward scattering parameter, the optical thickness, the visibility of area using the Radiative Transfer Equation for Spherical Media.

64. The method of claim 63, wherein the area is an airport.

65. The method of claim 63, wherein the area is a highway.

* * * * *